United States Patent
Davis et al.

(10) Patent No.: US 8,290,557 B2
(45) Date of Patent: Oct. 16, 2012

(54) IMPLANTABLE OPTICAL SENSOR AND METHOD FOR USE

(75) Inventors: Timothy J. Davis, Coon Rapids, MN (US); Jonathan P. Roberts, Coon Rapids, MN (US); James D. Reinke, Maple Grove, MN (US); Jonathan L. Kuhn, Ham Lake, MN (US); Shawn D. Knowles, St. Francis, MN (US)

(73) Assignee: Medtronic, Inc., Minneapolis, MN (US)

( * ) Notice: Subject to any disclaimer, the term of this patent is extended or adjusted under 35 U.S.C. 154(b) by 1342 days.

(21) Appl. No.: 11/955,025

(22) Filed: Dec. 12, 2007

(65) Prior Publication Data

US 2009/0156918 A1    Jun. 18, 2009

(51) Int. Cl.
*A61B 5/1455* (2006.01)
*A61B 5/02* (2006.01)

(52) U.S. Cl. ........ 600/310; 600/322; 600/323; 600/324; 600/500; 600/502

(58) Field of Classification Search .................. 600/310, 600/322–327, 331–333, 341–342, 500, 502; 607/6, 17
See application file for complete search history.

(56) References Cited

U.S. PATENT DOCUMENTS

| | | | |
|---|---|---|---|
| 3,985,449 A | 10/1976 | Patrin et al. | |
| 4,100,562 A | 7/1978 | Sugawara et al. | |
| 4,202,339 A | 5/1980 | Wirtzfeld et al. | |
| 4,467,807 A | 8/1984 | Bornzin | |
| 4,730,389 A | 3/1988 | Baudino et al. | |
| 5,010,381 A | 4/1991 | Shiba et al. | |
| 5,069,214 A * | 12/1991 | Samaras et al. | 600/323 |
| 5,144,381 A | 9/1992 | Furnyama et al. | |
| 5,833,603 A * | 11/1998 | Kovacs et al. | 600/317 |
| 5,902,326 A | 5/1999 | Lessar et al. | |
| 6,125,290 A | 9/2000 | Miesel et al. | |
| 6,198,952 B1 | 3/2001 | Miesel et al. | |
| 7,248,906 B2 * | 7/2007 | Dirac et al. | 600/310 |
| 2002/0179815 A1 | 12/2002 | Forke | |
| 2004/0176669 A1 | 9/2004 | Colvin et al. | |

(Continued)

FOREIGN PATENT DOCUMENTS

WO    W02006012737    2/2006

(Continued)

OTHER PUBLICATIONS

Miyazaki et al, "Using a Light-Emitting Diode as a High-Speed, Wavelength Selective Photodetector", Review of Scientific Instruments, AIP, Nov. 1, 1998, pp. 3751-3754, vol. 69, No. 11, Melville, NY, US.

Dietz et al, "Very Low-Cost Sensing and Communication Using Bidirectional LEDs", Internet Citation Http://www.merl.com/reports/docs/TR2003-35.pdf, Jul. 18, 2007, chapters 1 and 2.

(Continued)

*Primary Examiner* — Eric Winakur
*Assistant Examiner* — Chu Chuan (JJ) Liu
(74) *Attorney, Agent, or Firm* — Evans M. Mburu; Michael C. Soldner; Stephen W. Bauer

(57) ABSTRACT

An implantable medical device includes a hermetically sealed housing and a first light emitting diode (LED) enclosed within the housing configured to detect light corresponding to a selected light wavelength. A conductive element extends from the LED for carrying a current signal corresponding to the light detected by the LED, the intensity of the detected light being correlated to a change in a physiological condition in a body fluid volume or a tissue volume proximate the LED.

16 Claims, 6 Drawing Sheets

U.S. PATENT DOCUMENTS

2004/0220629 A1 11/2004 Kamath et al.
2005/0035304 A1* 2/2005 Colvin et al. .............. 250/458.1
2007/0015981 A1 1/2007 Benaron et al.

FOREIGN PATENT DOCUMENTS

| WO | WO2007119084 | 10/2007 |
| WO | WO2007144810 | 12/2007 |

OTHER PUBLICATIONS

Dasgupta et al, "Light Emitting Diode Based Flow-Through Optical Absorption Detectors", Talanta, Jan. 1, 2003, pp. 53-74, vol. 40, No. 1, Elmsford, NY, US.

International Search Report, PCT/US2008/085170, Feb. 23, 2009, 7 Pages.

* cited by examiner

IMPLANTABLE OPTICAL SENSOR AND METHOD FOR USE

REFERENCE TO RELATED APPLICATIONS

Cross-reference is hereby made to co-pending U.S. patent application Ser. No. 11/955,039 entitled "IMPLANTABLE OPTICAL SENSOR AND METHOD FOR MANUFACTURE" and U.S. patent application Ser. No. 11,955,056 entitled "IMPLANTABLE OPTICAL SENSOR AND METHOD FOR MANUFACTURE" both applications filed on even date herewith and incorporated herein by reference in their entirety.

TECHNICAL FIELD

The invention relates generally to implantable medical devices and, in particular, to an implantable optical sensor for sensing physiological conditions.

BACKGROUND

Implantable medical devices (IMDs) for monitoring a physiological condition and/or delivering a therapy include one or more physiological sensors. Physiological sensors used in conjunction with an IMD provide a signal related to a physiological condition from which a patient state or the need for a therapy can be assessed. Examples of such IMDs include heart monitors, pacemakers, implantable cardioverter defibrillators (ICDs), myostimulators, neurological stimulators, drug delivery devices, insulin pumps, glucose monitors, etc.

Optical sensors are employed in IMDs as physiological sensors configured to detect changes in light modulation by a body fluid or tissue measurement volume due to a change in a physiological condition in the body fluid or tissue. Such optical sensors can be used, for example, for detecting changes in metabolite levels in the blood, such as oxygen saturation levels or glucose level, or changes in tissue perfusion. Monitoring such physiological conditions provides useful diagnostic measures and can be used in managing therapies for treating a medical condition. For example, a decrease in blood oxygen saturation or in tissue perfusion may be associated with insufficient cardiac output or respiratory function. Thus monitoring such signals allows an implantable medical device to respond to a decrease in oxygen saturation or tissue perfusion, for example by delivering electrical stimulation therapies to the heart to restore a normal hemodynamic function. One example of an implantable optical sensor used for monitoring blood oxygen saturation is generally disclosed in commonly assigned U.S. Pat. No. 6,198,952 issued to Miesel, hereby incorporated herein by reference in its entirety. Cardiac pacemakers that respond to changes in blood oxygen saturation as measured by an optical sensor are generally disclosed in U.S. Pat. No. 4,202,339 issued to Wirtzfeld and in U.S. Pat. No. 4,467,807 issued to Bornzin, both of which patents are incorporated herein by reference in their entirety.

Implantable optical sensors typically include a set of light emitting diodes (LEDs), for example two or more LEDs, each emitting a different narrow band of light, and a photodetector for detecting emitted light that is scattered by blood or tissue back to the sensor. A current signal emitted by the photodetector in response to the scattered light incident on the photodetector is correlated to a physiological change in the adjacent body fluid or tissue. It is generally desirable to provide sensitive light detection to achieve reliable measurements and to minimize the size of such implantable sensors to minimize patient discomfort and to facilitate the ease of implantation procedures.

DETAILED DESCRIPTION

Figure 1:
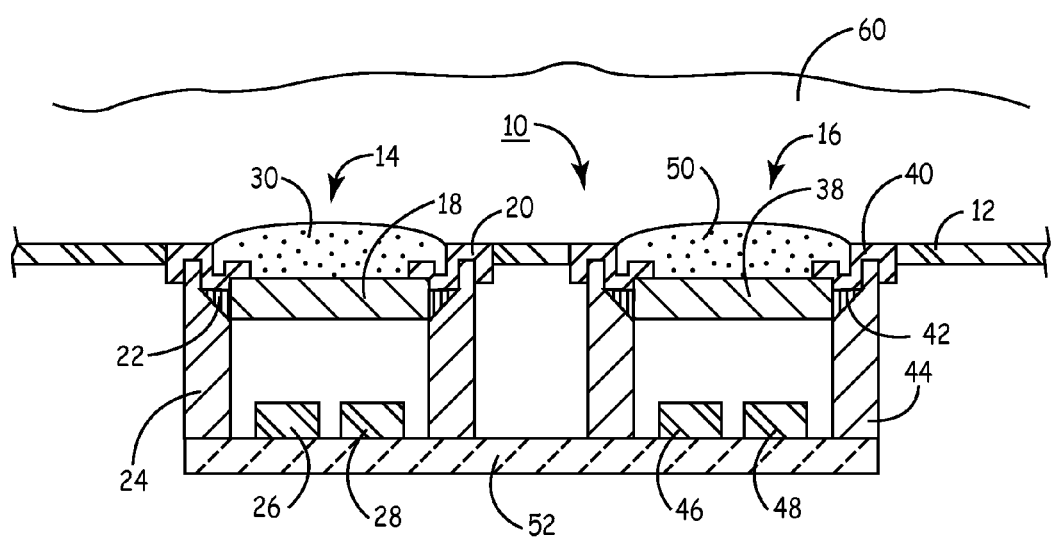
FIG. 1 is a side sectional view of a color selective optical sensor according to one embodiment of the invention.

In the following description, references are made to illustrative embodiments for carrying out the invention. It is understood that other embodiments may be utilized without departing from the scope of the invention. For purposes of clarity, the same reference numbers are used in the drawings to identify similar elements.

FIG. 1 is side sectional view of an optical sensor 10 according to one embodiment of the invention. Sensor 10 may be incorporated in the housing of an implantable medical device, such as in a subcutaneously implanted pacemaker or ICD housing, or carried by a medical electrical lead. Sensor 10 includes a light emitting portion 14, a light detecting portion 16, and a hermetically sealed capsule or housing 12 for enclosing optical sensor components. Each portion 14 and 16 includes a lens 18 and 38, respectively, for passing emitted light from the light emitting portion 14 and scattered light to the light detecting portion 16. Lens 18 and lens 38 are commonly formed from sapphire and are hermetically sealed with housing 12 using ferrules 20 and 40, respectively, bonded to lenses 18 and 38 at joints 22 and 42. Joints 22 and 42 may be gold braze joints or formed using a polymer adhesive depending on the ferrule material and other manufacturing processes used in fabricating sensor 10.

Housing 12 may be formed, for example, from titanium, stainless steel, ceramic, glass, or a rigid polymer. In one embodiment, housing 12 and ferrules 20 and 40 are each formed from titanium. Ferrules 20 and 40 are then welded within openings formed in housing 12 to maintain hermeticity of sensor 10. The optical window assembly generally disclosed in U.S. Pat. No. 5,902,326 (Lessar, et al.), hereby incorporated herein by reference in its entirety, may be implemented in embodiments of the present invention. Transparent polymeric seals 30 and 50 may be formed over lenses 18 and 38 and ferrules 20 and 40, respectively. Seals 30 and 50 may be formed, for example, from silicone rubber. Seals 30 and 50 protect gold braze joints 22 and 42 from the corrosive effects of bodily fluids and provide a smooth, convex surface that reduces the susceptibility of sensor 10 to blood clot formation and excessive tissue encapsulation over lenses 18 and 38.

Blood clot formation and tissue encapsulation reduces light transmission into and out of sensor 10.

The emitting portion 14 includes light sources embodied as LEDs 26 and 28. LEDs 26 and 28 are mounted on a printed circuit board 52 to enable the necessary connections for applying a voltage to each of LEDs 26 and 28 to cause light emission. A wall 24 surrounds the LEDs 26 and 28 to prevent scattering of light and promote transmission of light through lens 18 toward adjacent body fluid or tissue volume 60. Body fluid or tissue volume 60 may correspond to any bodily fluid, such as blood, or body tissue, such as skeletal muscle, neural tissue, myocardium, etc. Wall 24 may be formed from a rigid, non-transparent material, such as a liquid crystal polymer. Alternatively, wall 24 can be formed from other non-transparent materials, for example a polymer material formed as a molded component. Wall 24 is coupled to circuit board 52. Wall 24 may be coupled to printed circuit board 52 using a hard die coat dam holding wall 24 to the board 52.

The two LEDs 26 and 28 typically emit light corresponding to two different wavelengths or colors. In one embodiment, in which sensor 10 is used for sensing blood oxygen saturation, one of LEDs 26 and 28 emits red light and the other emits infrared light. In another embodiment, in which sensor assembly 10 is used for sensing tissue perfusion, a third LED may be included. Emitted light passes through lens 18 and enters body fluid or tissue volume 60. It is recognized that one or more LEDs may be included in light emitting portion 14. The number of LEDs and corresponding emission wavelengths will be selected according to the requirements of a particular application and will depend on the physiological condition being monitored.

The detecting portion 16 includes two light detectors embodied as LEDs 46 and 48. LEDs 46 and 48 are mounted on printed circuit board 52 to enable appropriate electrical connections to LEDs 46 and 48. LEDs are formed from a direct band-gap semiconductor that emits narrow spectrum light when electrically biased in the forward direction of the p-n junction. Instead of biasing LEDs 46 and 48 to emit light, LEDs 46 and 48 are biased to generate current upon exposure to light, allowing LEDs 46 and 48 to function as light detectors. A wall 44 surrounds the LEDs 46 and 48 to promote light traveling through lens 38 to fall on LEDs 46 and 48. Wall 44 may share a common side with wall 24 in some embodiments, and may be formed from rigid, opaque material, such as a liquid crystal polymer. Alternatively, wall 44 can be formed from other, non-rigid, materials, for example a polymer material formed as a molded component. Wall 44 may be attached to printed circuit board 52 using a hard die coat dam holding wall 44 to the board 52.

LEDs 46 and 48 are selected to match light emitting LEDs 26 and 28 such that one light-detecting LED 46 is sensitive to the same color of light emitted by LED 26 and the other light-detecting LED 48 is sensitive to the same color wavelength emitted by LED 28. In one embodiment, in which sensor assembly 10 is used for sensing blood oxygen saturation as described above, one of LEDs 26 and 28 is sensitive to red light and the other of LEDs 26 and 28 is sensitive to infrared light. In another embodiment, in which sensor assembly 10 is used for sensing tissue perfusion, a third LED may be included.

Light emitted from emitting portion 14 is scattered by the body fluid or tissue volume 60. Scattered light travels through lens 38 to LEDs 46 and 48. Scattered light that corresponds to wavelengths to which light-detecting LEDs 26 and 28 are responsive will cause the LEDs 46 and 48 to emit a current corresponding to the intensity of the received light, allowing sensor 10 to operate as a selective color sensor. Light modulation due to the physiological change results in a signal generated by the light detecting LEDs 46 and 48 that is correlated to the changing physiological condition. As such, light wavelengths scattered by body fluid or tissue volume 60 will cause an LED responsive to selected light wavelengths to emit a signal useful in estimating a change in a physiological condition in the body fluid or tissue volume 60. In an optical sensor for estimating oxygen saturation in blood, the intensity of red light scattered by the body fluid or tissue and detected by one of LEDs 46 and 48 is dependent on the concentration of oxygen in the body fluid or tissue. The intensity of infrared light scattered by the body fluid or tissue is independent of the concentration of oxygen. The scattered light detected by the LED 46 or 48 responsive to red light is normalized by the light detected by the other LED 46 or 48 responsive to infrared light to correct for variables such as tissue overgrowth and blood flow velocity or other artifacts.

Circuit board 52 is shown as a single circuit board on which both emitting portion 14 and detecting portion 16 are assembled. In alternative embodiments, separate circuit boards may be provided for each emitting and detecting portion. Although not shown in FIG. 1, it will be understood by one having skill in the art that the circuit board 52 includes integrated circuitry electrically coupled to LEDs 26 and 28 to deliver driver signals applied to LEDs 26 and 28 to activate LEDs 26 and 28. Likewise, integrated circuitry included on circuit board 52, or a separate circuit board, is coupled to light detecting LEDs 46 and 48 to receive the current emitted by LEDs 46 and 48 in response to scattered light incident on LEDs 46 and 48 and providing the signal to processing circuitry configured to perform an algorithm for detecting a change in a physiological condition using the signal. Integrated circuitry may include an analog-to-digital converter and flash memory for digitizing the analog signal and providing the digitized signal to processing circuitry.

Figure 2:
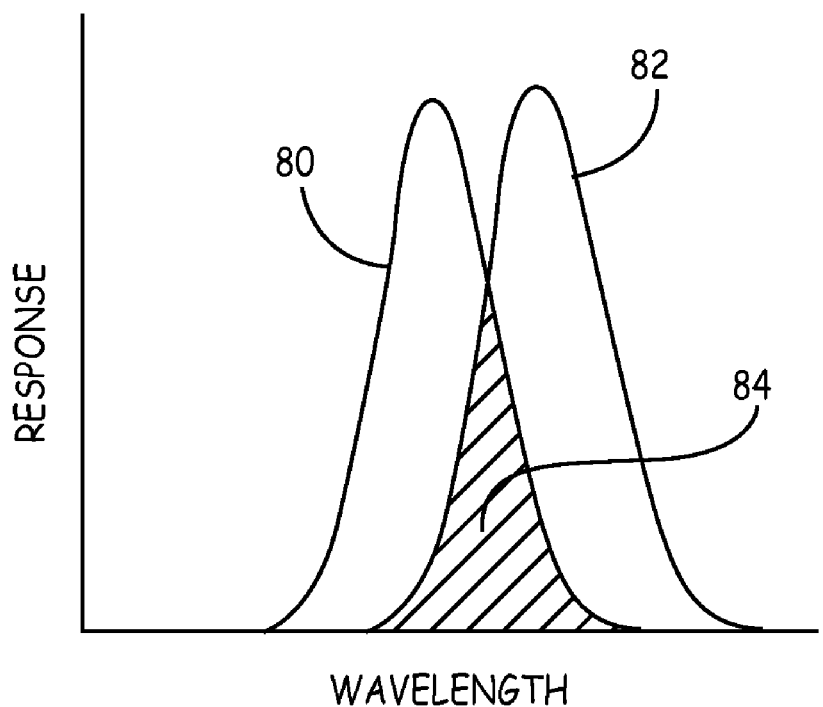
FIG. 2 is a plot of the relative light emission and light detection curves for a given LED.

FIG. 2 is a plot of the relative light emission and light detection curves for a given LED. The light emission curve 80, which indicates the bandwidth and relative intensity of light wavelengths emitted by an LED, is shifted relative to a light detection curve 82, which indicates the bandwidth and relative responsivity to light wavelengths detected by the same LED. It is recognized that the peak-emission wavelength of an LED used as a light emitter may be somewhat different than the peak-detection wavelength of the same LED used as a light detector. An overlap 84 between the emitted light spectrum and the detected light spectrum, however, for a given LED does allow for narrowband light detection in a selective color sensor.

Figure 3:
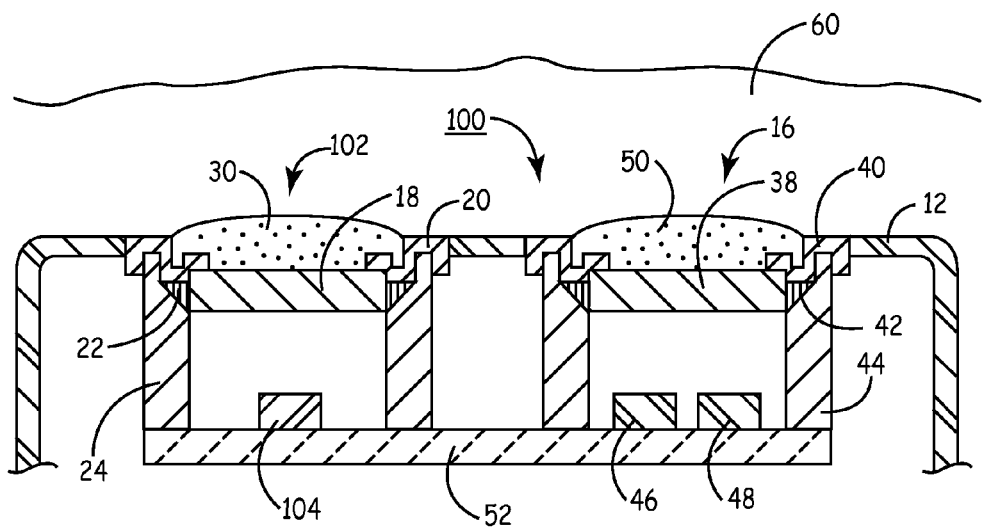
FIG. 3 is a side sectional view of an alternative embodiment of an optical sensor.

FIG. 3 is a side sectional view of an alternative embodiment of an optical sensor. In FIG. 3, elements indicated by an identical reference numerals correspond to like-numbered elements shown in FIG. 1. Sensor 100 includes a light emitting portion 102 and a light detecting portion 16. The light detecting portion 16 includes light detecting LEDs 46 and 48 as described above. The light emitting portion 102, however, includes a white light emitter 104 instead of LEDs. White light emitter 104, or another broadband light emitter, emits a wide spectrum of light wavelengths. Light scattered by tissue or body fluid volume 60 is received by light detecting portion 16. LEDs 46 and 48 are selected to be responsive to wavelengths associated with light modulated by a changing physiological condition of interest in body fluid or tissue volume 60. As such, while a wide spectrum of light is emitted from emitting portion 102, sensor 100 is selectively sensitive to narrow bandwidths of color wavelengths corresponding to the wavelength responsivity of LEDs 46 and 48.

Figure 4:
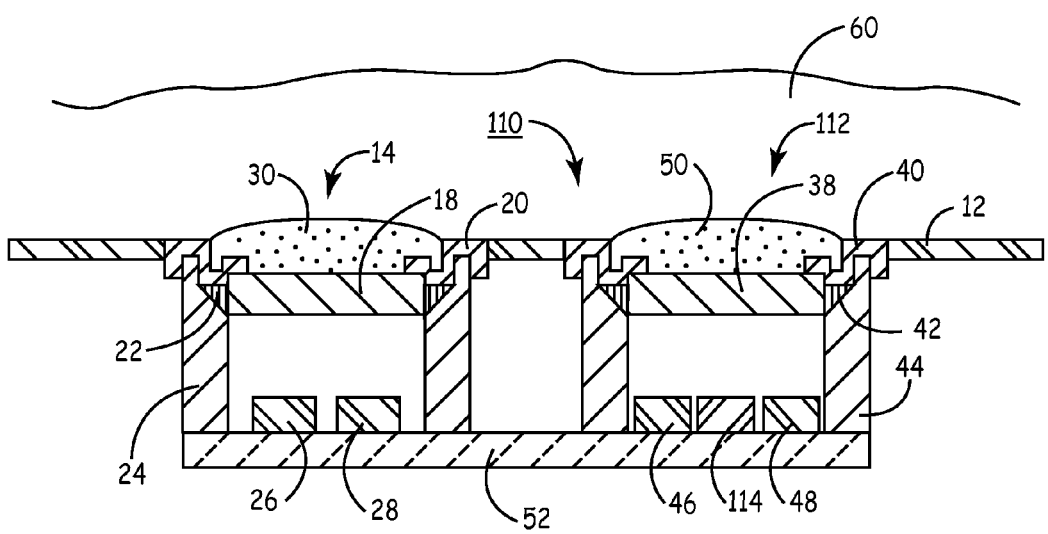
FIG. 4 is a side sectional view of yet another embodiment of a color selective optical sensor.

FIG. 4 is a side sectional view of yet another embodiment of a color selective optical sensor. As in FIG. 3, identically-numbered elements correspond to those shown in FIG. 1. In sensor 110, the light detecting portion 112 includes a photodetector 114 in addition to LEDs 46 and 48. As used herein, "photodetector" refers to any opto-electronic component responsive to a broad band of light wavelengths (thus not including LEDs which are responsive to a narrow band of wavelengths) and emit current in the presence of light. Examples of photodetectors include photoresistors or light dependent resistors, photodiodes, phototransistors, photovoltaic cells, or charge-coupled devices. Photodetector 114 is provided as a redundant detector for use in verifying color detection made by LEDs 46 and 48 and/or provides greater overall sensitivity of detecting portion 112. It is recognized that one or more LEDs provided for detecting light may be combined with a photodetector in a light detecting portion of a color selective optical sensor to provide redundancy and increased light sensitivity.

Figure 5:
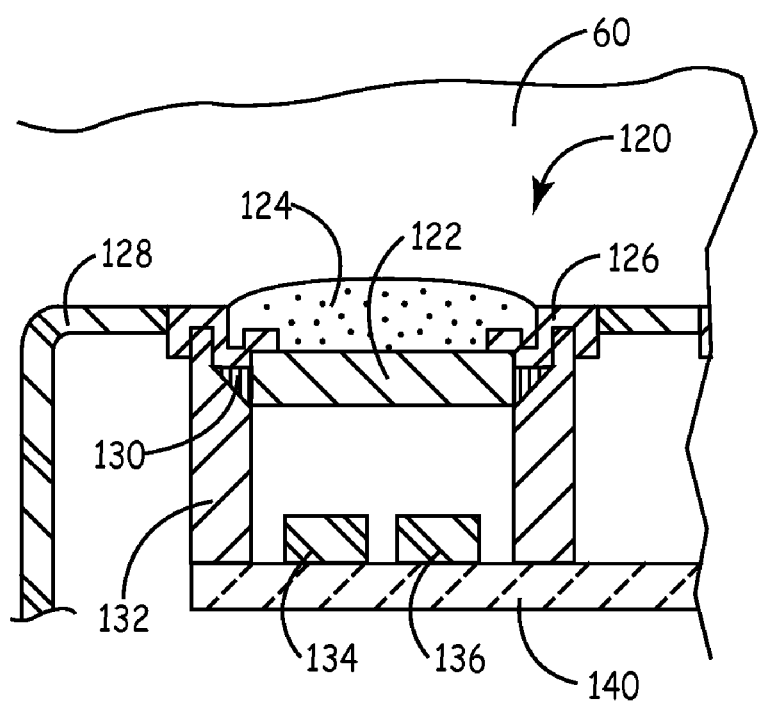
FIG. 5 is a side sectional view of a color-selective optical sensor including only a light detecting portion.

FIG. 5 is a side sectional view of a color-selective optical sensor including only a light detecting portion. Sensor 120 includes a lens 122 bonded to a ferrule 126 at joint 130. Ferrule 126 is hermetically sealed in an opening formed in housing 128. A polymer seal 124 may be formed over lens 122. A wall 132 is bonded to circuit board 140 upon which one or more LEDs 134 and 136 are mounted. LEDs 134 and 136 are electrically configured to detect light. In particular, LEDs 134 and 136 are responsive to a narrow bandwidth of light color such that sensor 120 functions as a selective color sensor. Sensor 120 is responsive to ambient light penetrating body fluid or tissue volume 60. As such, sensor 120 is generally adapted for implantation at a subcutaneous location that will be exposed to ambient light passing through the tissue to the implanted sensor 120. Sensor 120 may optionally include a light emitting portion as described in conjunction with previous embodiments such that light detecting portion responds to ambient light and/or emitted light scattered by the body fluid or tissue volume 60. An ambient light source may be natural sun light, room light or a light applied to the skin of the patient. Ambient light penetrating through body fluid or tissue volume 60 will be scattered by the body fluid/tissue volume 60 toward LEDs 134 and 136. A current will be emitted by LEDs 134 and 136 in response to the scattered ambient light incident on sensor 120. The current signal will be correlated to modulated light wavelengths which fall into the narrow light spectrum to which LEDs 134 and 136 are responsive. The intensity of these light wavelengths are modulated due to a physiological change in the body fluid or tissue.

Figure 6:
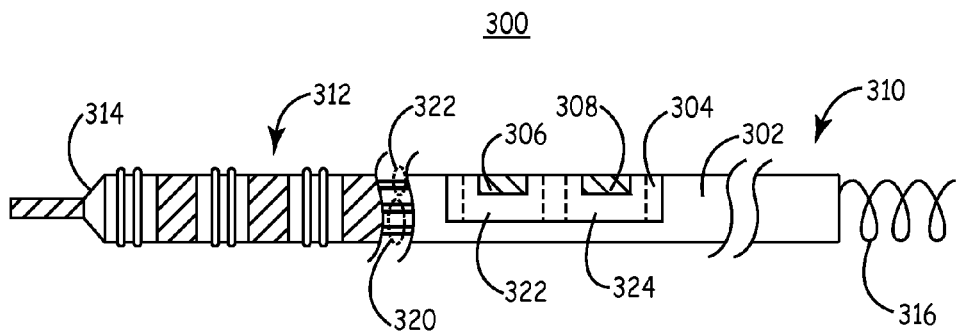
FIG. 6 is a plan view of a medical lead including an optical sensor according to one embodiment of the invention.

FIG. 6 is a plan view of a medical lead including an optical sensor according to one embodiment of the invention. Lead 300 includes an elongated body 302 extending between a proximal end 312 and a distal end 310. A sensor 304 is positioned along lead body 302, typically near distal end 310. Sensor 304 includes at least two windows 306 and 308 through which emitted light and scattered light travels from/to an emitting portion 322 and a detecting portion 324, respectively, of sensor 304. Windows 306 and 308 correspond, for example, to the polymer seals 30 and 50 overlaying glass lenses 18 and 38 as shown in FIG. 1.

Lead body 304 carries separately insulated conductor pairs 322 and 320 between a proximal connector assembly 314 and sensor 304. Conductor pair 322 is provided for carrying drive signals from proximal connector assembly 314 to light emitting sources (LEDs and/or or white light or other wideband light sources) in emitting portion 322. Conductor pair 320 is provided for carrying current generated by LEDs included in detecting portion 324 to proximal connector assembly 314. Connector assembly 314 is coupled to an implantable medical device to thereby couple the sensor 304 to associated sensor driver/signal processing circuitry (not shown in FIG. 6) included in the medical device.

Lead 300 is shown having a distal fixation member 316 for anchoring the position of distal end 310 at a targeted implant location. In some embodiments, fixation member 316 may serve as an electrode and be coupled to an insulated conductor extending to proximal connector assembly 314. In various embodiments lead 300 may include other sensors and/or electrodes. As such, it is recognized that the particular configurations of lead body 302, conductors carried by the lead body and the proximal connector assembly 314 will depend on the particular configuration of electrodes and sensors carried by lead 300.

Figure 7:
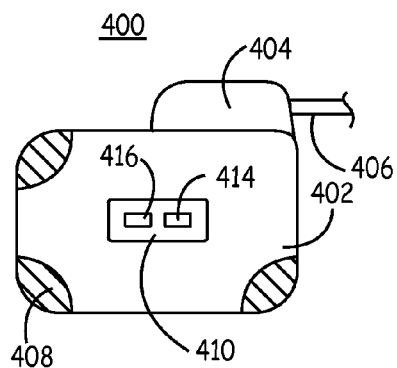
FIG. 7 is a plan view of an IMD in which a selective color sensor is incorporated in the housing of the IMD.

FIG. 7 is a plan view of an IMD 400 in which a selective color sensor 410 is incorporated in the housing 402 of device 400. IMD 400 includes hermetically sealed housing 402, a connector block 404 and may include an electrode array 408 or other physiological sensors incorporated in housing 402. Sensor 410 is hermetically sealed within an opening in IMD housing 402 such that windows 414 and 416 associated with light emitting and light detecting portions of sensor 410 are exposed to adjacent tissue or body fluid when the IMD 400 is implanted in a subcutaneous, submuscular, transvenous, intracardiac or other internal body location. Electrical connections (not shown) between sensor 410 and IMD circuitry (not shown) enclosed in housing 402 allow the sensing function of sensor 410 to be controlled by IMD 400 and signal processing of signals responsive to detected light to be performed by IMD 400.

Lead 406 is shown coupled to connector block 404 allowing any electrodes or sensors carried by lead 406 to be electrically coupled to circuitry enclosed within housing 402. Lead 406 may correspond to lead 300 shown in FIG. 7 such that a lead-based optical sensor, including light detecting LEDs, can be coupled to IMD 400. It is recognized that in alternative embodiments, IMD 400 may be provided as a leadless device, without connector block 400, including only sensors/electrodes incorporated in housing 402. IMD 400 may be embodied as a monitoring-only device or may include therapy delivery capabilities, such as electrical stimulation or drug delivery capabilities, responsive to signals generated by sensor 410.

Figure 8:
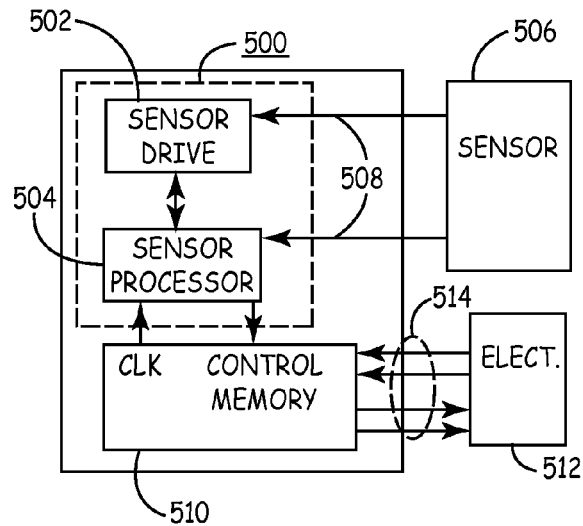
FIG. 8 is a functional block diagram of circuitry included in an IMD system that includes a color-selective optical sensor.

FIG. 8 is a functional block diagram of circuitry included in an IMD system that includes a color-selective optical sensor. Sensor module 500 includes a sensor driver circuit 502 and sensor processor circuit 504. As used herein, the term "module" refers to an application specific integrated circuit (ASIC), an electronic circuit, a processor (shared, dedicated, or group) and memory that execute one or more software or firmware programs, a combinational logic circuit, or other suitable components that provide the described functionality. Conductor elements 508 extending from an optical sensor 506, which may correspond to any of the sensor embodiments described herein or variations thereof, provide connection to sensor driver circuit 502 and sensor processor circuit 504 via any necessary connector elements, feedthroughs, etc. Sensor driver circuit 502 provides the operational power for optical sensor 506 and controls the timing of optical sensor operation. Sensor processor circuit 504 receives optical sensor signal output and processes the signal output to estimate a change in a physiological condition, such as blood oxygen saturation, glucose saturation, tissue perfusion or any other condition causing alterations in light modulation by the measurement body fluid or tissue volume. Sensor driver circuit 502 and sensor processor circuit 504 may operate as generally disclosed in U.S. Pat. No. 4,730,389 (Baudino et al.), hereby incorporated herein by reference in its entirety.

Operation of sensor module 500 is controlled by control module 510 which may include a microprocessor and associated memory, a clock signal (CLK) and power supply. Control module 510 controls other IMD functions, including data storage and other sensing and/or therapy delivery functions, which may be performed in conjunction with electrodes 512 coupled to control module 510 via conductors 514. Detailed descriptions of such circuitry included in an implantable medical device and its operation are generally provided in the above-incorporated '952 patent to Miesel.

Figure 9:
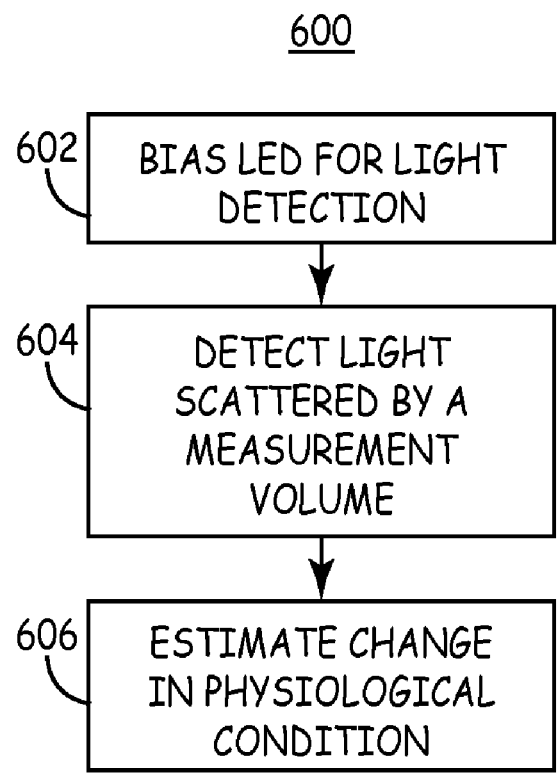
FIG. 9 is a flow chart of a method for selectively sensing color using an implantable optical sensor.

FIG. 9 is a flow chart of a method for selectively sensing color using an implantable optical sensor. At block 602, one or more LEDs included in an optical sensor are biased for sensing light rather than emitting light. At block 604, light scattered by a measurement volume in a body fluid or tissue adjacent the optical sensor is detected by the LED(s), causing the LED to emit a current correlated to the intensity of narrow band light detected by the LED(s).

At block 606, a change in a physiological condition is estimated from the current signal generated by the LED(s). Changes in the monitored physiological condition cause modulation of light in the fluid or tissue volume, allowing changes in the physiological condition to be detected by selectively sensing modulated wavelengths using LED(s).

Thus, an optical sensor having selective color sensitivity for use with implantable medical devices has been presented in the foregoing description with reference to specific embodiments. It is appreciated that various modifications to the referenced embodiments may be made without departing from the scope of the invention as set forth in the following claims.

The invention claimed is:

1. An implantable medical device, comprising:
a hermetically sealed housing;
a first light emitting diode (LED) enclosed within the housing and configured to detect ambient light penetrating through body tissue of a patient corresponding to a first selected light wavelength;
a sensor module; and
a conductive element for carrying a current signal from the first LED to the sensor module, the current signal corresponding to an intensity of the detected ambient light, wherein the sensor module estimates, based on the intensity of the ambient light detected by the first LED, a change in a physiological condition in one of a body fluid volume and a tissue volume proximate the first LED, and wherein the intensity of the ambient light detected by the first LED is correlated to the change in the physiological condition.

2. The device of claim 1 further comprising an elongated body having a proximal end, the housing being positioned along the elongated body and the sensor module being coupled to the proximal end, wherein the conductive element comprises an insulated conductor extending between the proximal end and the housing for carrying a current signal responsive to the light detection from the first light emitting diode to the proximal end.

3. The device of claim 1 further comprising a second LED for detecting light having a second selected light wavelength.

4. The device of claim 3 wherein the light detected by the second LED is correlated to the change in the physiological condition.

5. The device of claim 1 further comprising a second LED for emitting light having a wavelength corresponding to the first selected light wavelength.

6. The device of claim 1 further comprising a wideband light emitting device for emitting light detected by the first LED.

7. The device of claim 1 wherein the first selected wavelength corresponds to red light and further comprising a second light emitting diode for detecting a second selected light wavelength corresponding to infrared light.

8. The device of claim 3 wherein the light detected by the first LED is normalized by the light detected by the second LED.

9. A method for sensing color for use in an implantable medical device, comprising:
detecting ambient light penetrating through body tissue of a patient scattered by one of a body fluid volume and tissue volume using a first light emitting diode (LED) responsive to a first selected light wavelength; and
estimating a change in a physiological condition in the one of the body fluid volume and the tissue volume in response to the ambient light,
wherein an intensity of the ambient light having the first selected light wavelength is correlated to the change in the physiological condition.

10. The method of claim 9 further comprising detecting light using a second LED responsive to a second selected light wavelength.

11. The method of claim 10 wherein an intensity of the light detected by the second LED is correlated to the change in the physiological condition.

12. The method of claim 9 further comprising emitting light having a wavelength corresponding to the first selected light wavelength using a second LED.

13. The method of claim 9 further comprising emitting light having a wideband of wavelengths.

14. The method of claim 9 wherein the first selected wavelength corresponds to red light, and further comprising detecting a second selected light wavelength corresponding to infrared light using a second light emitting diode.

15. The method of claim 10 wherein the light detected by the first LED is normalized by the light detected by the second LED.

16. An implantable medical device, comprising:
a hermetically sealed housing;
an opto-electronic device configured for sensing a narrow band of light wavelengths of ambient light passing through a body of a patient;
a sensor module; and
a conductive element for carrying a current signal from the opto-electronic device to the sensor module, the current signal corresponding to an intensity of the ambient light, wherein the sensor module estimates, based on the intensity of the ambient light detected by the opto-electronic device, a change in a physiological condition in one of a body fluid volume and a tissue volume proximate the opto-electronic device,
the intensity of the sensed light being correlated to the change in the physiological condition.

* * * * *